(12) United States Patent
Aronhime et al.

(10) Patent No.: US 7,183,272 B2
(45) Date of Patent: Feb. 27, 2007

(54) CRYSTAL FORMS OF OXCARBAZEPINE AND PROCESSES FOR THEIR PREPARATION

(75) Inventors: Judith Aronhime, Rehovot (IL); Ben-Zion Dolitzky, Petach Tiqva (IL); Yana Berkovich, Jerusalem (IL); Nissim Garti, Ramot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 193 days.

(21) Appl. No.: 10/074,181

(22) Filed: Feb. 12, 2002

(65) Prior Publication Data

US 2003/0004154 A1 Jan. 2, 2003

Related U.S. Application Data

(60) Provisional application No. 60/268,314, filed on Feb. 12, 2001.

(51) Int. Cl.
*A61P 25/16* (2006.01)
*A61P 25/08* (2006.01)
*A61K 31/55* (2006.01)
*C07D 223/18* (2006.01)

(52) U.S. Cl. .................... 514/217; 540/589
(58) Field of Classification Search .......... 424/489, 424/464, 451; 514/217; 540/589
See application file for complete search history.

(56) References Cited

U.S. PATENT DOCUMENTS

| | | | |
|---|---|---|---|
| 3,716,640 A | 2/1973 | Schindler | 424/244 |
| 4,452,738 A | 6/1984 | Aufderhaar | 260/239 D |
| 4,559,174 A | 12/1985 | Aufderhaar | 260/239 D |
| 5,658,900 A | 8/1997 | Boireau et al. | 514/217 |
| 5,808,058 A | 9/1998 | Milanese | 540/588 |
| 6,670,472 B2 | 12/2003 | Ansari et al. | 540/589 |

FOREIGN PATENT DOCUMENTS

WO    WO 03/106414    12/2003

*Primary Examiner*—Brenda Coleman
(74) *Attorney, Agent, or Firm*—Kenyon & Kenyon LLP

(57) ABSTRACT

The present invention provides for new crystal forms of oxcarbazepine, more particularly oxcarbazepine Forms B, C, D and E. The present invention further provides processes for preparation of these forms. Form B is prepared by evaporating the solvents from a solution of oxcarbazepine in toluene and dichloromethane. Form B is also obtained by immediately cooling the solution of oxcarbazepine and toluene. Cooling the same solution at a slower rate, but still fairly rapidly, results in oxcarbazepine Form C. Cooling the same solution at even a slower rate results in another Form, oxcarbazepine Form D. Oxcarbazepine Form E, a solvate of chloroform, is obtained by precipitating a solution of oxcarbazepine and chloroform. The present invention also provides processes for converting one of the newly discovered crystal forms of oxcarbazepine into another crystal form, including Form A, which is in the prior art. These conversions may occur by storage at ambient temperature, by heating one particular Form or treatment with a protic solvent.

68 Claims, 5 Drawing Sheets

CRYSTAL FORMS OF OXCARBAZEPINE AND PROCESSES FOR THEIR PREPARATION

CROSS-REFERENCE TO RELATED APPLICATIONS

This application claims the benefit under 35 U.S.C. 1.119 (e) of U.S. provisional application No. 60/268,314, filed on Feb. 12, 2001.

FIELD OF THE INVENTION

This invention relates to new crystal forms of oxcarbazepine and processes for their preparation.

BACKGROUND OF THE INVENTION

Oxcarbazepine (10-oxo-10,11-dihydro-5H-dibenz[b,f]azepine-5-carboxamide) of the general formula:

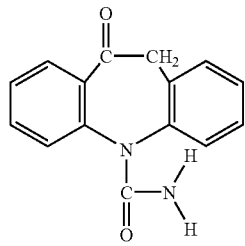

has valuable therapeutic benefits and acts as a central nervous system depressant. Currently it is being marketed as TRILEPTAL®, for treatment of epilepsy. According to the prescribing information for TRILEPTAL®, the pharmacological benefit of oxcarbazepine is primarily exerted through the 10-hydroxy metabolite of oxcarbazepine. In vitro studies indicate that the metabolite blocks voltage sensitive sodium channels, which results in the stabilization of hyperexcited neural membranes, inhibition of repetitive neuronal firing, and diminution of propagation of synaptic impulses. These actions are thought to be important in the prevention of seizure spread in the brain. U.S. Pat. No. 5,658,900, incorporated herein by reference, further teaches the use of oxcarbazepine to treat Parkinson's disease. TRILEPTAL® is administered in a dosage units of 150 mg, 300 mg and 600 mg.

U.S. Pat. Nos. 3,716,640; 4,452,738; 4,559,174 and 5,808,058 are hereby incorporated by reference for their disclosures of processes for preparing oxcarbazepine.

The present invention relates to the solid state physical properties of oxcarbazepine prepared by any of the disclosed or other methods. These properties can be influenced by controlling the conditions under which the oxcarbazepine is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular crystalline form of a substance. The crystalline form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by powder X-ray crystallography, solid state $^{13}C$ NMR spectrometry and infrared spectrometry.

According to U.S. Pat. No. 3,716,640, oxcarbazepine may be prepared from 10-methoxy-5H-dibenz[b, f]azepine-5-carboxamide of formula:

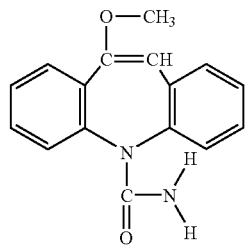

by hydrolysis with hydrochloric acid. Oxcarbazepine with a melting point of 215–216° C. was obtained after recrystallization from ethanol.

U.S. Pat. No. 4,559,174 contains numerous examples of a process of preparing oxcarbazepine via a 5-cyano-10-nitro-5H-dibenz[b,f]acepine intermediate. In these examples, the product was obtained as a precipitate from the mother liquor and in some instances recrystallized and in other instances washed or slurried with solvent to remove impurities. Solvents from which oxcarbazepine was precipitated or recrystallized are chlorobenzene, acetic acid/water, water, isopropanol, acetonitrile and methanol/water.

U.S. Pat. No. 5,808,058 teaches that oxcarbazepine may be prepared from N-carbamoylization of 10-methoxyminostilbene with sodium or potassium cyanate in the presence of a strong non-aqueous acid, followed by mild aqueous acid hydrolysis of the methoxy group. In the examples, oxcarbazepine was recrystallized from dimethylacetamide, cyclohexanone, ethylcellosolve, 2:1 DMF:water, methanol and dioxane.

The oxcarbazepine that is formulated into the commercial product TRILEPTAL® is designated herein as oxcarbazepine Form A. Oxcarbazepine Form A is a white to faintly orange crystalline powder. It is slightly soluble in solvents such as chloroform, dichloromethane, acetone and methanol, and practically insoluble in solvents ethanol, ether and water. Due to its low solubility, crystallization of oxcarbazepine from water is impracticable unless the crystallization is carried on from a hot solution. Crystallization from water and various organic solvents such as acetonitrile, THF, ethyl acetate, EtOH/toluene, dichloromethane, DMA, DMF, cyclohexane, cyclohexanone, alcohols, chloroform, water/DMA, DMA/hexane, DMF/EtOH, DMA, and acetone consistently produce the prior art Form A.

There is a need for discovery of accessible but previously unknown polymorphic forms of a pharmaceutically useful compound because it provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

Four new polymorphic and pseudopolymorphic forms of oxcarbazepine have now been discovered. They can be differentiated by their powder X-ray diffraction ("PXRD") patterns and thermogravimetric analysis ("TGA").

SUMMARY OF THE INVENTION

According to one aspect, the present invention provides oxcarbazepine Form B. According to another aspect, the present invention provides for oxcarbazepine having a PXRD diffraction pattern with peaks at about 11.9, 14.4, 20.0, 23.0, 25.1±0.2 degrees two-theta.

According to another aspect, the present invention provides a process for preparing oxcarbazepine Form B comprising the steps of preparing a solution of oxcarbazepine in a mixture of dichloromethane and toluene, and evaporating the toluene and dichloromethane mixture.

According to another aspect, the present invention provides a process for preparing oxcarbazepine Form B comprising the steps of preparing a solution of oxcarbazepine in toluene, heating the solution, cooling the solution at a rate of 60° C. min$^{-1}$ or above to cause formation of a precipitate, and separating the precipitate.

According to another aspect, the present invention relates to oxcarbazepine Form C. The present invention relates to oxcarbazepine characterized by PXRD peaks at about 11.7, 21.7, 23.2, 24.4±0.2 degrees two-theta.

In another aspect, the present invention provides a process for preparing oxcarbazepine Form C comprising the steps of preparing a solution of oxcarbazepine in toluene, heating the solution, cooling the solution at a rate of from about 20 to 60° C. min−1 to cause formation of a precipitate and separating the precipitate.

In another aspect, the present invention relates to oxcarbazepine Form D. The present invention also relates to oxcarbazepine characterized by PXRD peaks at about 11.7, 14.2, 24.3±0.2 degrees two-theta.

In another aspect, the present invention provides a process for preparing oxcarbazepine Form D comprising the steps of preparing a solution of oxcarbazepine in toluene, and evaporating the toluene leaving a residue of oxcarbazepine Form D.

In another aspect, the present invention provides for oxcarbazepine chloroform solvate Form E.

In another aspect, the present invention relates to oxcarbazepine chloroform solvate. The present invention also relates to oxcarbazepine solvate characterized by PXRD peaks at about 14.5, 15.0, 18.2, 21.4, 22.9, 24.0, 25.8, 26.0±0.2 degrees two-theta.

In another aspect, the present invention provides a process for preparing oxcarbazepine solvate Form E comprising causing the formation of a precipitate from a solution of oxcarbazepine in chloroform, and separating the precipitate.

In another aspect, the present invention provides a process for preparing oxcarbazepine Form A comprising heating oxcarbazepine solvate Form E.

In another aspect, the present invention provides a process for preparing oxcarbazepine Form A comprising heating oxcarbazepine Form B.

In another aspect, the present invention provides a process for the preparation of oxcarbazepine Form C comprising storing oxcarbazepine Form B at ambient temperature.

In another aspect, the present invention provides a process for preparing oxcarbazepine Form A comprising contacting the oxcarbazepine selected from the group consisting of oxcarbazepine Form B, oxcarbazepine Form C and oxcarbazepine Form D with a protic solvent.

In another aspect, the present invention relates to a pharmaceutical composition comprising oxcarbazepine selected from the group consisting of oxcarbazepine Form B, oxcarbazepine Form C, oxcarbazepine Form D and oxcarbazepine Form E, and a pharmaceutically acceptable excipient.

DETAILED DESCRIPTION OF THE INVENTION

Figure 1:
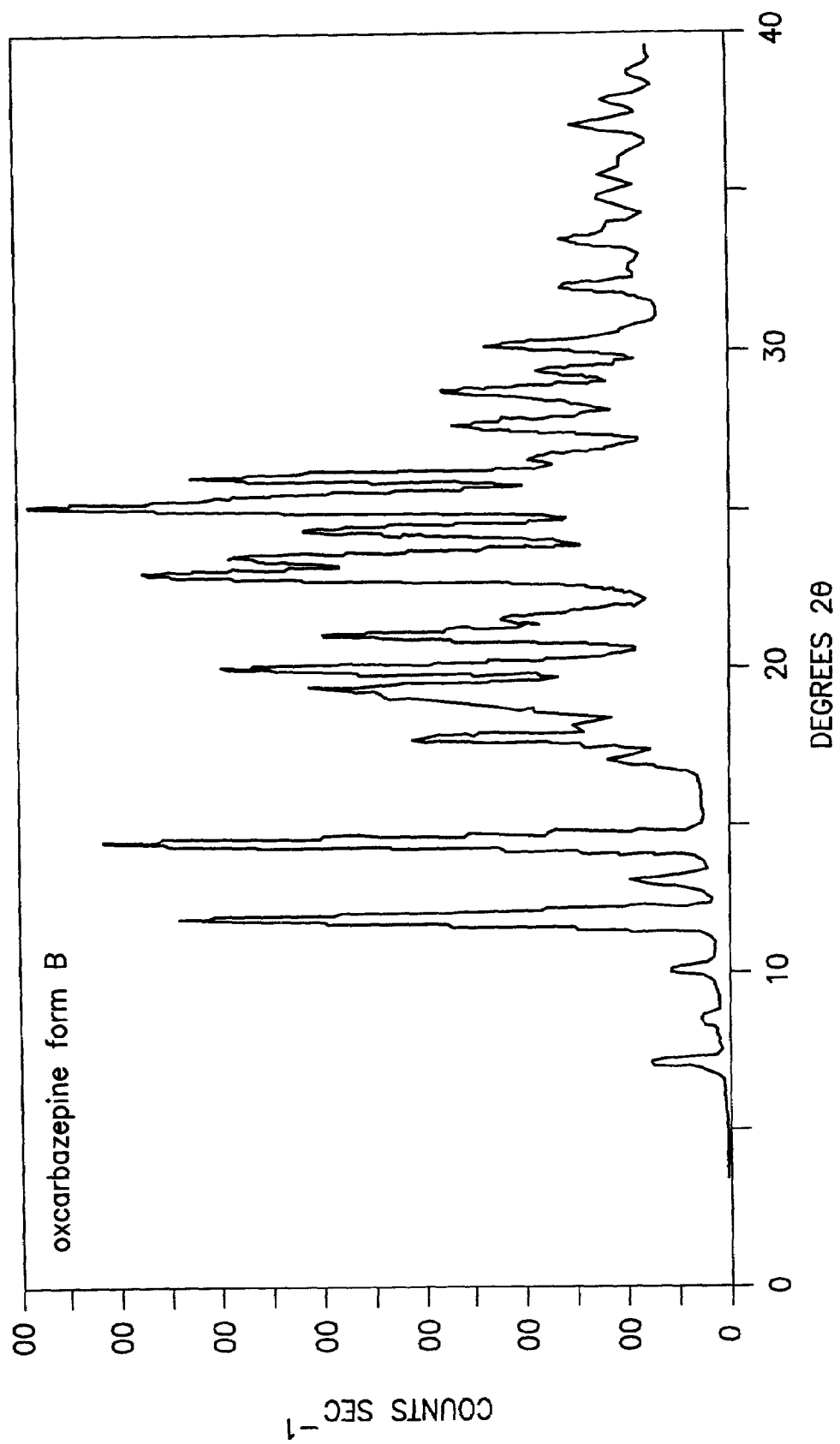
FIG. 1 is a PXRD pattern for oxcarbazepine Form B.

As used herein, the term "solution" refers to a mixture, which preferably is homogeneous. A homogeneous mixture may not result from the initial addition of a solute to a solvent, but only after subsequent heating of the mixture.

It has now been found that new crystal forms, differentiated from prior art Form A, can be obtained by crystallization induced by rapid cooling or evaporation of oxcarbazepine solutions in toluene, toluene: dichloromethane mixtures and chloroform.

Four novel crystal forms of oxcarbazepine have been isolated and characterized. These forms are distinguished by their PXRD patterns. The DSC profile of all the samples shows a melting peak concomitant to decomposition at about 230° C.

Generally, in PXRD, compounds can be characterized by the position and intensity of diffraction peaks. However, the intensity of the peaks can differ from sample to sample, due to, among other things, orientation effects. In some crystal habits certain orientations are preferred which enhance some diffraction peaks and reduce others. We describe below as "major" or "strongest" peaks the largest peaks in the samples we measured. However, these peaks may not be the largest peaks in some samples or preparations due to the orientation effects. The peak positions, on the other hand, are largely unaffected by orientation effects.

The present invention provides a novel form of oxcarbazepine designated Form B. The oxcarbazepine Form B may be characterized by a PXRD pattern (FIG. 1) with peaks at about 11.9, 14.4, 20.0, 23.0, 25.1±0.2 degrees two-theta. More particularly, the oxcarbazepine Form B may be characterized by a PXRD pattern with peaks at about 11.9, 14.4, 17.7, 19.4, 20.0, 21.1, 23.0, 24.0, 24.4, 25.1, 26.0±0.2 degrees two-theta.

Form B may be obtained by preparing a solution of oxcarbazepine in dichloromethane, adding the solution to toluene and evaporating the mixed solvent at a controlled rate. Oxcarbazepine is preferably dissolved in dichloromethane in a weight ratio of from about 1:66 to about 1:116, more preferably about 1:110. After dissolution of the oxcarbazepine, toluene is added, preferably in an amount of from about 9.4 ml g$^{-1}$ dichloromethane to about 12.8 ml g$^{-1}$ dichloromethane, more preferably about 8.5 ml g$^{-1}$. Oxcarbazepine crystallizes during evaporation of the solvent mixture into Form B when the solvent is evaporated at from about 1/30 to about 1/50 of its initial volume per minute, more preferably about 1/40 its initial volume per minute. This rate of evaporation can be obtained using a conventional rotary evaporator with aspirator vaccum, without warming the flask. Preferably, oxcarbarzepine is added to the dichloromethane in such a manner that a homogeneous mixture is obtained.

Form B may be prepared by an alternative process that comprises the steps of preparing a solution of oxcarbazepine in toluene, heating the solution, cooling the solution at a rate of 60° C. min$^{-1}$ or above to cause formation of a precipitate, and separating the precipitate.

Oxcarbazepine is first added to toluene to form a solution, preferably in a ratio of from about 8 mg to about 10 mg oxcarbazepine per gram of toluene. The solution is then heated, preferably to reflux for a sufficient time to substantially dissolve the oxcarbazepine in toluene.

The solution is then cooled very rapidly to about 0° C., i.e. at a rate of about 60° C. min$^{-1}$ or faster. Such rapid cooling may be acheived by dipping the sample in salt ice bath at a temperature of −13° C. Rapidly cooling the solution leads to the formation of the apparently kinetically favored product oxcarbazepine Form B. Oxcarbazepine precipitates from the solution in less than about five minutes, and is then separated. Preferably, a filter is used to separate the oxcarbazepine Form B. To filter, the solution may be passed through paper, glass fiber or other membrane material or a clarifying agent such as celite.

The present invention also provides oxcarbazepine Form C. Oxcarbazepine Form C is characterized by a PXRD pattern (FIG. 2) with peaks at about 11.7, 21.7, 23.2, 24.4±0.2 degrees two-theta. More particularly, Form C is characterized by peaks at about 11.7, 17.0, 18.0, 21.7, 23.2, 24.4, 26.0±0.2 degrees two-theta.

The present invention also provides a process for preparing oxcarbazepine Form C comprising the steps of preparing a solution of oxcarbazepine and toluene, heating the solution, cooling the solution at a rate of 60° C. min$^{-1}$ or above to cause formation of a precipitate, and separating the precipitate.

Oxcarbazepine is added to toluene to form a solution which is subsequently heated. Preferably, oxcarbazepine is added in an amount of from about 7.3 mg ml$^{-1}$ to about 9.0 mg ml$^{-1}$, more preferably about 8.1 mg ml$^{-1}$. The solution is preferably heated to from about 25° C. to about reflux, with temperatures at or near reflux being most preferred. One skilled in the art may appreciate that the solution may be completely homogeneous only after the heating step.

After heating for about 10 minutes, the solution is then cooled rapidly. The solution is cooled at a slower rate than is used to obtain Form B, but rapidly enough to allow for the formation of oxcarbazepine Form C as major product. Preferably, the solution is cooled at a rate of about 20° C. to about 60° C. per minute, and most preferably at a rate of about 40° C. per minute. To cool the solution at a rate of 40 C per minute, an ice water bath with a temperature of 0° C. may be used.

The solution is preferably cooled to about 0° C. One skilled in the art may appreciate that other temperatures may also suffice as long as they allow for the substantial formation of Form C. After cooling, a precipitate forms, which is then separated. Preferably, the precipitate is separated with a filter. To filter, the solution may be passed through paper, glass fiber or other membrane materials, or a clarifying agent such as celite.

The present invention also provides oxcarbazepine Form D. Oxcarbazepine Form D is characterized by a PXRD pattern (FIG. 3) with peaks at about 11.7, 14.2, 24.3±0.2 degrees two-theta.

The present invention provides a process for preparing oxcarbazepine Form D comprising the steps of preparing a solution of oxcarbazepine in toluene, and evaporating the toluene from the solution.

Oxcarbazepine is first added to toluene to form a solution. Oxcarbazepine is preferably added in an amount of from about 8.5 to about 9.5 milligrams per gram of toluene, more preferably about 9.1 mg g$^{-1}$.

The solution is then preferably heated to completely dissolve the oxcarbazepine. The solution is preferably refluxed for a short amount of time, about five minutes, though a different of temperature and amount of time may also achieve the same result. One skilled in the art may appreciate that the solution may become completely homogeneous only after the heating step.

After heating, the solution is then preferably cooled to decrease the solubility of oxcarbazepine in the toluene. The solution is cooled at a slower rate than the processes resulting in Forms B and C. The solution is cooled at a rate of 20° C. min$^{-1}$ and below, more preferably at a rate of about 10° C. min$^{-1}$ to about 20° C. min$^{-1}$, and most preferably at a rate of 15° C. min$^{-1}$. The solution is cooled in such a way that a precipitate does not substantially form during cooling.

The solution is preferably cooled to from about 0° C. to about room temperature, most preferably to about 0° C. One skilled in the art may appreciate that other temperatures may achieve the same result.

After cooling, the toluene is removed by evaporation. The toluene may be evaporated under ambient or reduced pressure, or optionally heated to accelerate the evaporation. After evaporation, a residue remains which PXRD analysis has confirmed is oxcarbazepine Form D.

The process for the preparation of Form B in Example 1 and the process for the preparation of Form D are similar. To prepare Form D, oxcarbazepine is first added to toluene and then the toluene is evaporated. To prepare Form B, oxcarbazepine is first dissolved in dichloromethane and is added to toluene as a solution. The mixed solvent is then removed by evaporation to obtain Form B.

The present invention also provides oxcarbazepine as a solvate of chloroform. The oxcarbazepine solvate of the present invention is characterized by a PXRD pattern (FIG. 4) with peaks at about 14.5, 15.0, 18.2, 21.4, 22.9, 24.0, 25.8, 26.0±0.2 degrees two-theta. More particularly, the present invention provides for oxcarbazepine chloroform solvate Form E.

This form contains about 27% solvent, which corresponds to a % solvate of ¾ chloroform. The solvent content was measured by TGA, and a weight loss of 27% was seen between 30° C. and 90° C. This desolvatation is also observed in the DSC as an endotherm in the temperature range of about 40° C. to 90° C.

The present invention also provides a process for preparing oxcarbazepine solvate Form E comprising causing formation of a precipitate from a solution of oxcarbazepine and chloroform, and separating the precipitate. The conditions used are different than that of producing Form A by crystallization from chloroform, for instance dissolution at reflux and cooling at 10° C. min$^{-1}$ rate.

Oxcarbazepine is first dissolved in chloroform to form a solution. Oxcarbazepine is preferably added in an amount of from about 6.8 to about 8.0 milligrams per gram of chloroform, more preferably about 7.3 mg g$^{-1}$. The solution is then preferably heated to increase the amount of oxcarbazepine taken up by the chloroform. Preferably, the solution is completely homogeneous after the heating step. The solution is preferably heated from about 50° C. to about 60° C., and most preferably to about 55° C.

After heating, the solution is cooled. Preferably, the solution is cooled to a temperature at or below room temperature. Most preferably, the solution is cooled to about 16° C. The solubility of chloroform for oxcarbazepine decreases as the solution is cooled. To allow the solution to be cooled to a low temperature of about 16° C. without premature precipitation, the solution may first be cooled to a first temperature, and after a while to a second, lower temperature. Preferably, the solution is first cooled to about 25° C., and then to below room temperature. After cooling, a precipitate forms. The precipitate may be separated using a filter. Before filtering, the solution may be allowed to warm. Preferably, the solution is warmed to about 25° C.

The present invention also provides for processes that convert one form of oxcarbazepine into another form of oxcarbazepine. Form A may be obtained by heating oxcarbazepine solvate Form E at elevated temperatures between 40° C. and 80° C., preferably 60° C., for a period of 2 hours to 10 hours, preferably 4 hours. One skilled in the art may appreciate that Form E may transform to Form A under different conditions, and that the optimal conditions may be discovered with routine experimentation.

The present invention also provides a process for transforming Form B to Form C. It was found that Form B transforms to Form C at from about 20 to about 30° C., i.e. at about room temperature. The transformation is gradual and prolonged, and may occur over several months. One skilled in the art may appreciate that the optimal conditions and time for transformation may be discovered through routine experimentation.

The present invention also provides a process for transforming Form B to Form A. At about ambient temperature, Form B transforms to Form C. One skilled in the art would appreciate that such a transition may also occur at temperatures above and below ambient temperature, and that by routine experimentation the boundary of the temperature range may be determined. At higher temperatures, between 60° C. and 120° C., preferably 60° C., a transformation from form B to form A occurs after a few hours, as determined by the temperature. The temperature at which Form B transforms to Form A rather than Form C may be determined by routine experimentation. One skilled in the art may appreciate that the rate and extent of the transformation varies with the conditions and the amount of time under which the transformation occurs.

The present invention also provides a process for transforming Forms B, C, and D to Form A. It was found that Forms B, C or D may transform readily to the prior art Form A by slurry in protic solvents like ethanol or water for a period between several hours and several days, preferably for a period of 24 hours. One skilled in the art may appreciate that other protic solvents may be used and the optimal conditions may be determined through routine experimentation.

The pharmaceutical compositions of the present invention have valuable therapeutic benefits and act as a central nervous system depressant. The pharmaceutical compositions of the present invention may be used to treat epilepsy by preventing or reducing the extent of seizures. The pharmacological benefit of the compositions is primarily exerted through the 10-monohydroxy metabolite of oxcarbazepine. In vitro studies indicate that the metabolite blocks voltage sensitive sodium channels, which results in stabilization of hyperexcited neural membranes, inhibition of repetitive neuronal firing, and diminution of propagation of synaptic impulses. The phamaceutical compositions of the present invention may also be used to treat Parkinson's disease.

Pharmaceutical compositions of the present invention contain oxcarbazepine Form B, C, D and/or E, optionally in mixture with other Form(s), or amorphous oxcarbazepine and/or active ingredients. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form such as a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, clopidogrel hydrogensulfate and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, only they are not subjected to a final tableting step.

The solid unit dosage forms of the present invention preferably contain about 150, 300 or 600 mg of oxcarbazepine. The unit dosage form as used herein refers to the amount of the various forms of oxcarbazepine contained in the vehicle of administration, such as a tablet or a capsule. Most preferably, the unit dosage form of the present invention is administered as a tablet.

The tablet of the present invention is preferably film-coated and contains the following inactive ingredients: colloidal silicon dioxide; crospovidone; hydroxypropyl methylcellulose; magnesium stearate; microcrystalline cellulose; polyethylene glycol; talc and titanium dioxide; yellow iron oxide.

The liquid unit dosage forms of the present invention contain about 300 mg of oxcarbazepine in a suspension with 5 mL of liquid. Most preferably, the suspension is administered orally and has about 60 mg of oxcarbazepine for every milliliter of liquid.

The oral suspension of the present invention preferably contains the following inactive ingredients: ascorbic acid; dispersible cellulose; ethanol; macrogol stearate; methyl parahydroxybenzoate; propylene glycol; propyl parahydroxybenzoate; purified water; sodium saccharin; sorbic acid; sorbitol; yellow-plum-lemon aroma.

The characterization of crystalline phases were performed using Phillips PW 1710 Diffractometer. Thermograviometric analysis (TGA) was produced using Mettler TG50 equipped with Mettler TC11 TA processor. Differential Scanning calorimetry (DSC) was performed using Mettler DSC 30 apparatus. FTIR spectra were recorded using Nicolet Avatar 360 spectrometer.

One skilled in the art may appreciate that other unit dosages may be made as necessary in a routine fashion.

EXAMPLES

Example 1

Preparation of Form B

Oxcarbazepine (0.15 g) was dissolved in dichloromethane (20 g) at room temperature. After complete dissolution, the solution was added to toluene (170 mL). After stirring for 5 minutes the solvent was evaporated at the rate of 5 g min.$^{-1}$ until dryness. The resulting material was analyzed by PXRD and found to be form B.

Example 2

Preparation of Form B

Oxcarbazepine (0.3 g) was dissolved in toluene (33 g) at room temperature. After reflux for 5 minutes the reaction mixture was cooled immediately to 0° C. After 5 minutes, the suspension was filtered under reduced pressure. The resulting material was analyzed by PXRD and found to be Form B.

Example 3

Preparation of Form C

Oxcarbazepine (0.3 g) was dissolved in toluene (33 g) at room temperature. After reflux for 10 minutes the reaction mixture was cooled to 0° C. at the rate of 40° C. per minute. After 5 minutes, the suspension was filtered under reduced pressure. The resulting material was analyzed by PXRD and found to be Form C.

Example 4

Preparation of Form D

Oxcarbazepine (0.3 g) was dissolved in toluene (33 g) at room temperature. After reflux for 5 minutes the reaction mixture was cooled to 0° C. After 5 minutes, the solvent was evaporated. The resulting material was analyzed by PXRD and found to be Form D.

Example 5

Preparation of solvated Form E

Oxcarbazepine (1.1 g) was dissolved in chloroform (150 g) at room temperature. After heating to about 55° C. for 5 minutes the reaction mixture was cooled to 21.5° C., and after 8 hours the reaction mixture was cooled to 16° C. After 48 hours the suspension was heated to 25° C., and filtered under reduced pressure. The resulting material was analyzed by PXRD and found to be solvated form E.

Example 6

Preparation of Form A from Form E

Oxcarbazepine solvate Form E was heated to a temperature of 60° C. and maintained at that temperature for 4 hours. The resulting material was analyzed by PXRD, which showed oxcarbazepine Form A.

Example 7

Preparation of Form A from Form B

Oxcarbazepine Form B was heated to a temperature of about 60° C. and was maintained at that temperature for five hours. The resulting material was analyzed by PXRD, which showed oxcarbazepine Form A.

Example 8

Preparation of Form A from Form B

Oxcarbazepine Form B was suspended in ethanol for 24 hours. The product was analyzed by PXRD and determined to be Form A.

Example 9

Preparation of Form A from Form C

Oxcarbazepine Form C was suspended in ethanol for 24 hours. The product was analyzed by PXRD and determined to be Form A.

Example 10

Preparation of Form A from Form D

Oxcarbazepine Form D was suspended in water for 24 hours. The product is analyzed by PXRD and is determined to be Form A.

Example 11

Preparation of Form C from Form B

Oxcarbazepine Form B was stored at an ambient temperature. The resulting material was analyzed by PXRD and found to be Form C.

Having described the invention with reference to particular preferred embodiments and illustrated it with examples, those in the art may appreciate modifications to the invention as described and illustrated that do not depart from the spirit and scope of the invention as disclosed in the specification.

What is claimed is:

1. Crystalline oxcarbazepine, wherein the oxcarbazepine has a PXRD diffraction pattern with peaks at about 11.9, 14.4, 20.0, 23.0, 25.1±0.2 degrees two-theta.

2. The oxcarbazepine of claim 1 having a PXRD diffraction pattern with peaks at about 11.9, 14.4, 17.7, 19.4, 20.0, 21.1, 23.0, 24.0, 24.4, 25.1, 26.0±0.2 degrees two-theta.

3. The oxcarbazepine of claim 2 having a PXRD diffraction pattern substantially as depicted in FIG. 1.

4. A process for preparing the oxcarbazepine of claim 1 comprising the steps of:
   a) preparing a solution of oxcarbazepine in a mixture of dichioromethane and toluene, and
   b) evaporating the toluene and the dichloromethane leaving the oxcarbazepine as a residue.

5. The process of claim 4, wherein the solution is prepared by dissolving oxcarbazepine in dichloromethane and adding the dichloromethane to toluene.

6. Crystalline oxcarbazepine having a PXRD diffraction pattern with peaks at about 11.9, 14.4, 20.0, 23.0, 25.1±0.2 degrees two-theta prepared by 30 the process of claim 4.

7. A process for preparing the oxcarbazepine of claim 1 comprising the steps of:

a) preparing a solution of oxcarbazepine in toluene;
b) heating the solution;
c) cooling the solution at a rate of 60° C. min$^{-1}$ or above to cause formation of a precipitate; and
d) separating the precipitate.

8. The process of claim 7, wherein the solution is heated to about reflux.

9. The process of claim 7, wherein the solution is cooled to a temperature of about 0° C.

10. Crystalline oxcarbazepine having a PXRD diffraction pattern with peaks at about 11.9, 14.4, 20.0, 23.0, 25.1±0.2 degrees two-theta prepared by the process of claim 7.

11. Crystalline oxcarbazepine, wherein the oxcarbazepine has a PXRD diffraction pattern with peaks at about 11.7, 21.7, 23.2, 24.4±0.2 degrees two-theta.

12. The oxcarbazepine of claim 11 having a PXRD diffraction pattern with peaks at about 11.7, 17.0, 18.0, 21.7, 23.2, 24.4, 26.0±0.2 degrees two-theta.

Figure 2:
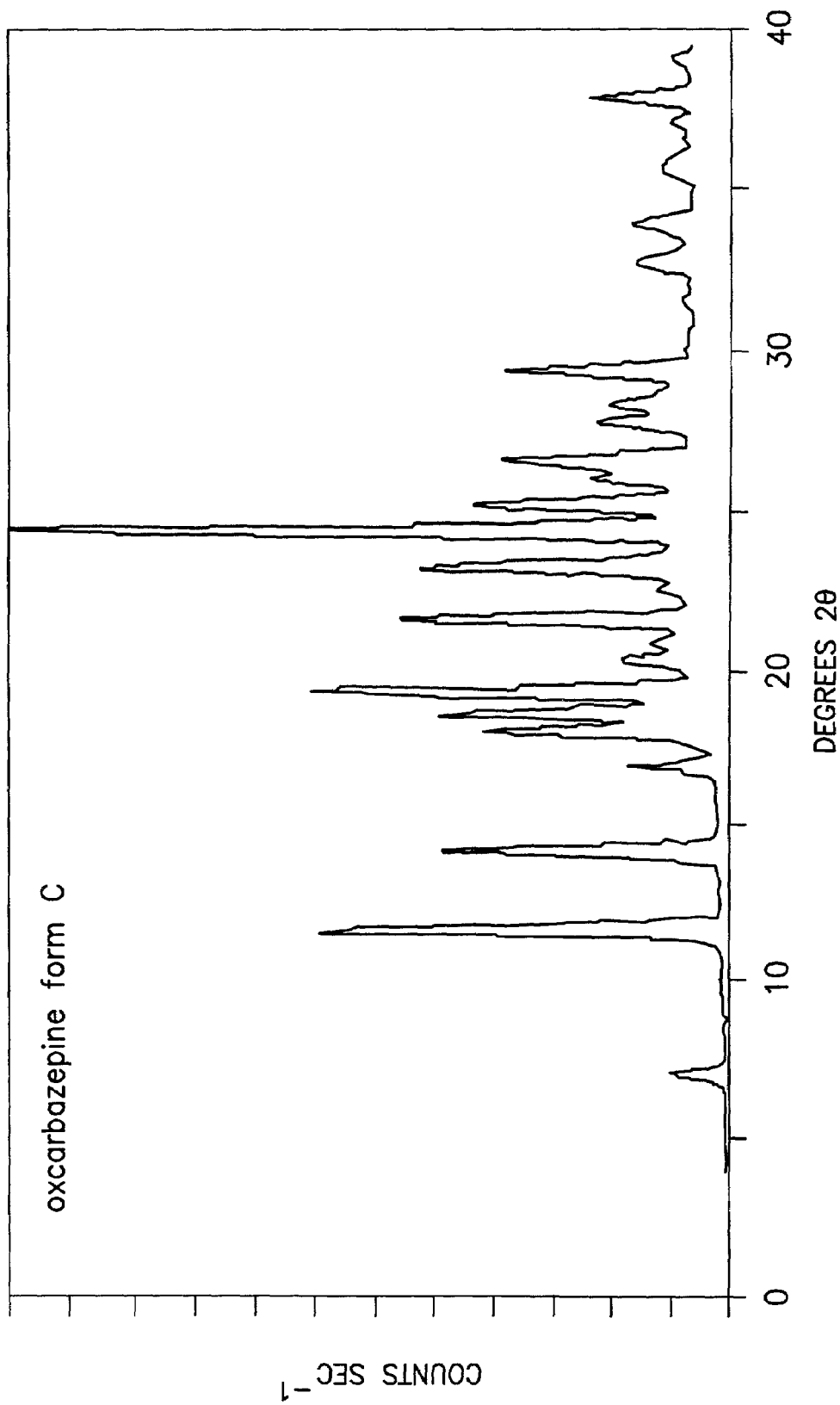
FIG. 2 is a PXRD pattern for oxcarbazepine Form C.

13. The oxcarbazepine of claim 12 having a PXRD diffraction pattern substantially as depicted in FIG. 2.

14. A process for preparing the oxcarbazepine of claim 11 comprising the steps of:
a) preparing a solution of oxcarbazepine in toluene;
b) heating the solution;
c) cooling the solution at a rate of from about 20 to 60° C. min.$^{-1}$ to cause formation of a precipitate; and
d) separating the precipitate.

15. The process of claim 14, wherein the solution is cooled at a rate of about 40° C. per minute.

16. The process of claim 14, wherein the solution is cooled to about 0° C.

17. The process of claim 14, wherein the solution is heated to about reflux.

18. Crystalline oxcarbazepine having a PXRD diffraction pattern with peaks at about 11.7, 21.7, 23.2, 24.4±0.2 degrees two-theta prepared by the process of claim 14.

19. Crystalline oxcarbazepine, wherein the oxcarbazepine has a PXRD diffraction pattern with peaks at about 11.7, 14.2, 24.3±0.2 degrees two-theta.

Figure 3:
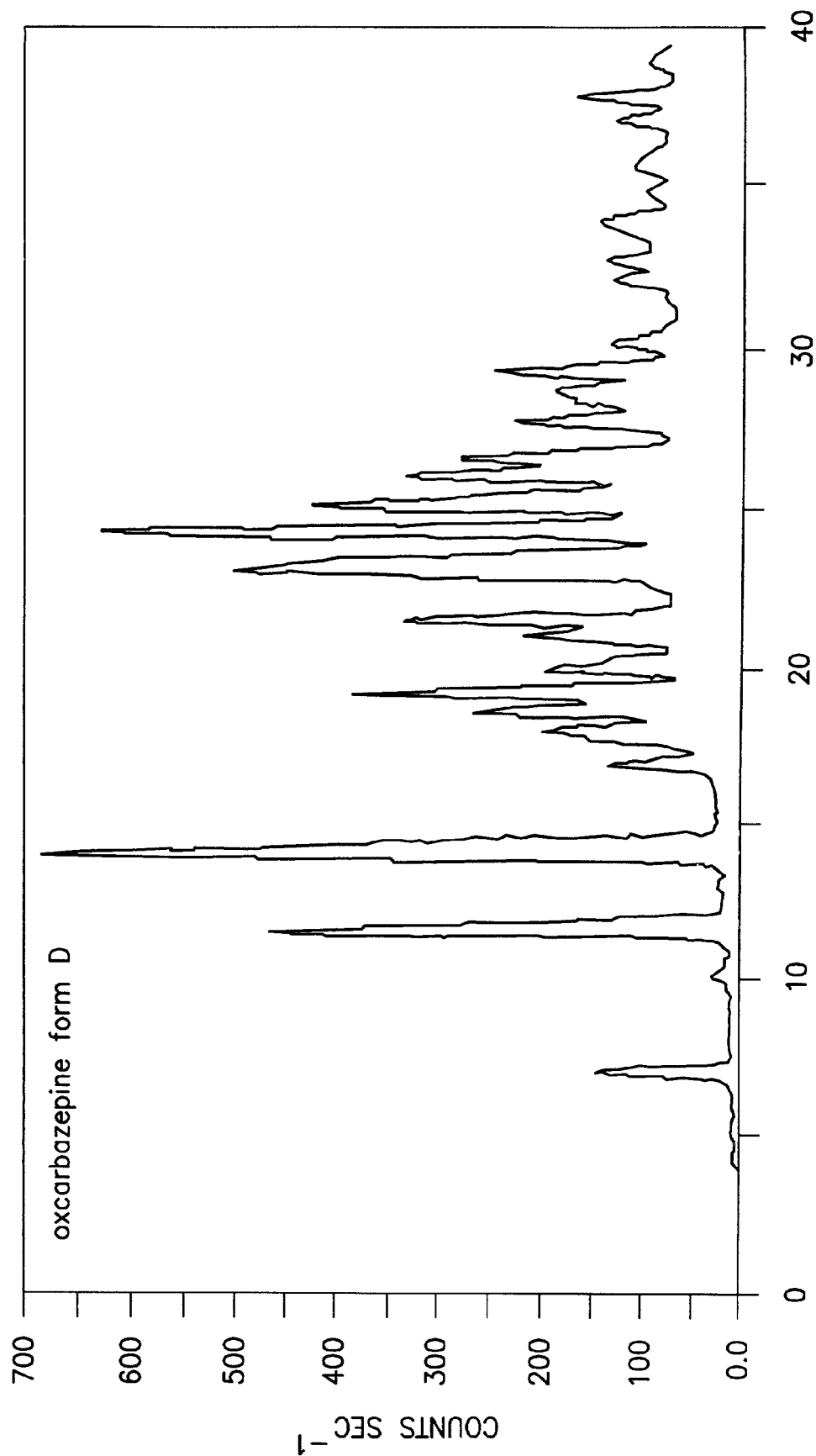
FIG. 3 is a PXRD pattern for oxcarbazepine Form D.

20. The oxcarbazepine of claim 19 having a PXRD diffraction pattern substantially as depicted in FIG. 3.

21. A process for preparing the oxcarbazepine of claim 19 comprising the steps of:
a) preparing a solution of oxcarbazepine in toluene; and
b) evaporating the toluene leaving a residue of the oxcarbazepine.

22. The process of claim 21, further comprising a step of heating the solution before evaporating.

23. The process of claim 22, wherein the solution is heated to about reflux.

24. The process of 22, further comprising cooling the heated solution before evaporating.

25. The process of claim 24, wherein the solution is cooled to about 0° C.

26. The process of claim 21, further comprising a step of cooling the solution.

27. The process of claim 26, wherein the solution is cooled to about 0° C.

28. The process of claim 21, wherein the toluene is removed from the solution by evaporation.

29. Crystalline oxcarbazepine having a PXRD diffraction pattern with peaks at about 11.7, 14.2, 24.3±0.2 degrees two-theta prepared by the process of claim 21.

30. An oxcarbazepine chloroform solvate.

31. A crystalline oxcarbazepine chloroform solvate, wherein the oxcarbazepine has a PXRLD diffraction pattern with peaks at about 14.5, 15.0, 18.2, 21.4, 22.9, 24.0, 25.8, 26.0±0.2 degrees two-theta.

Figure 4:
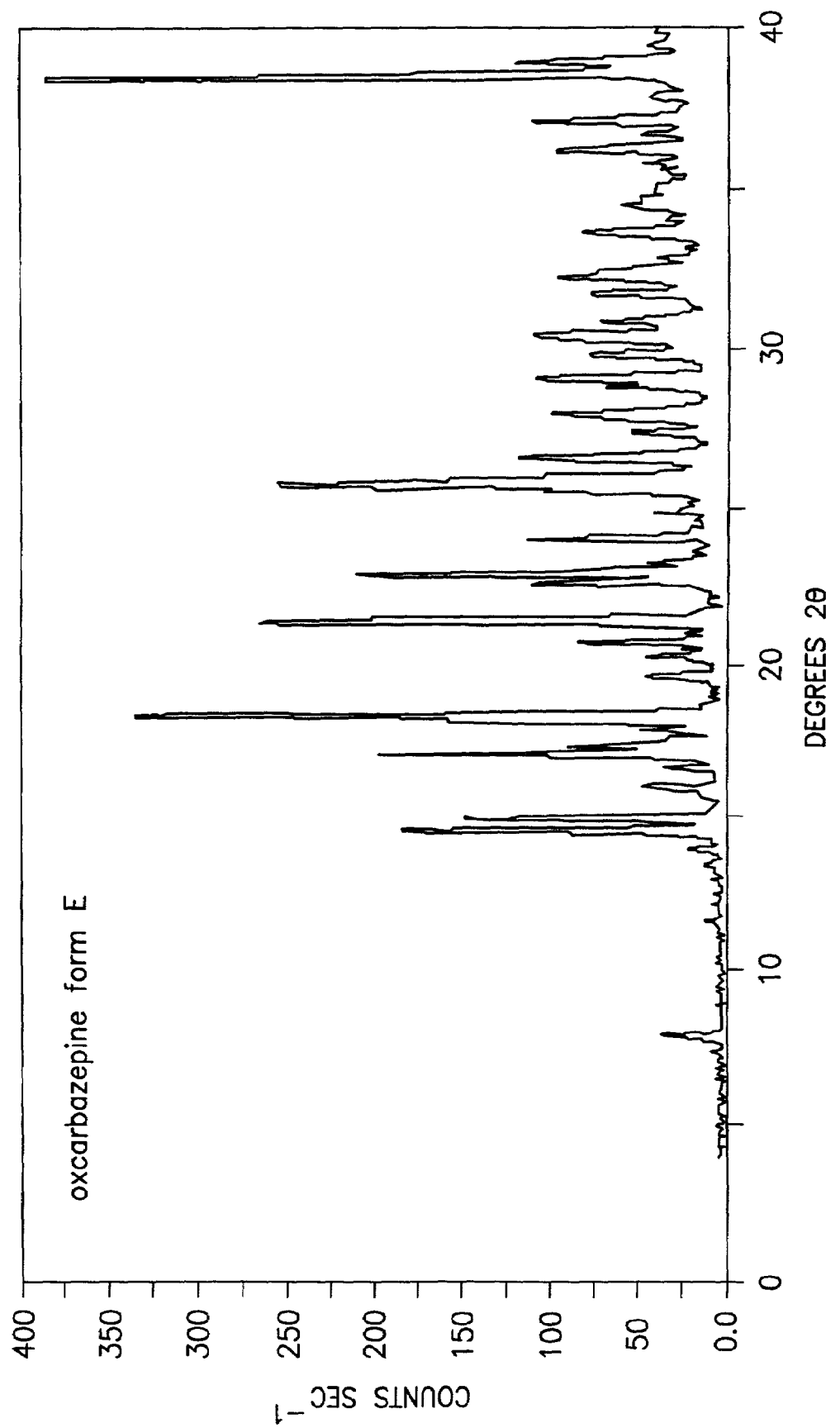
FIG. 4 is a PXRD pattern for oxcarbazepine Form E.

32. The oxcarbazepine chloroform solvate of claim 31, wherein the oxcarbazepine has a PXRD diffraction pattern substantially as depicted in figure 4.

33. The oxcarbazepine chloroform solvate of claim 30 containing about a 27 weight % chloroform.

34. A process for preparing oxcarbazepine chloroform solvate comprising:
a) causing formation of a precipitate from a solution of oxcarbazepine in chloroform, and
b) separating the precipitate.

35. The process of claim 34, further comprising a step of heating the solution before causing formation of the precipitate.

36. The process of claim 35, further comprising a step of cooling the heated solution, whereby cooling causes formation of the precipitate.

37. The process of claim 35, wherein the solution is heated to an elevated temperature of from about 50° C. to about 60° C.

38. The process of claim 37, wherein the solution is heated to an elevated temperature of about 55° C.

39. The process of claim 37, wherein the heated solution is cooled to a reduced temperature of from about 10° C. to about 20° C.

40. The process of claim 39, wherein the reduced temperature is about 16° C.

41. The oxcarbazepine chloroform solvate produced by the process of claim 34.

Figure 5:
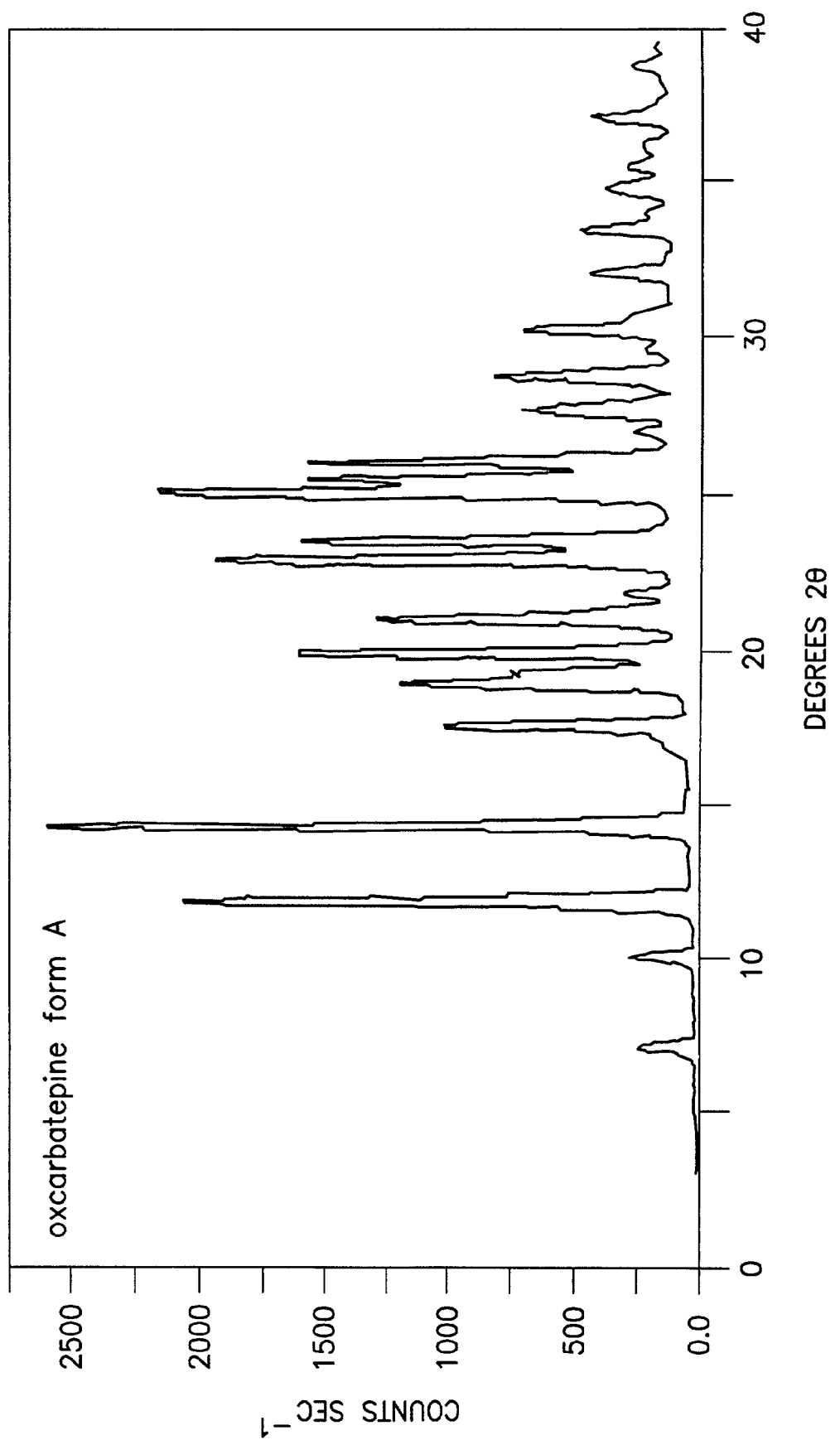
FIG. 5 is a PXRD pattern of oxcarbazepine Form A.

42. A process for preparing crystalline oxcarbazepine having a PXRD diffraction pattern substantially as depicted in FIG. 5 comprising:
a) providing the oxcarbazepine chloroform solvate of claim 31,
b) heating the oxcarbazepine chloroform solvate, and
c) recovering the oxcarbazepine.

43. The process of claim 42, wherein the oxcarbazepine solvate is heated to an elevated temperature in the range of from about 40° C. to about 80° C.

44. The process of claim 43, wherein the elevated temperature is about 60° C.

45. A process for preparing crystalline oxcarbazepine having a PXRD diffraction pattern substantially as depicted in FIG. 5 comprising
a) providing crystalline oxcarbazepine having a PXRD diffraction pattern with peaks at about 11.9, 14.4, 20.0, 23.0, 25.1±0.2 degrees two-theta,
b) heating the oxcarbazepine, and
c) recovering the oxcarbazepine.

46. The process of claim 45, wherein the oxcarbazepine is heated to an elevated temperature in the range of from about 60° C. to about 120° C.

47. The process of claim 46, wherein the elevated temperature is about 60° C.

48. A process for the preparation of crystalline oxcarbazepine having a PXRD diffraction pattern with peaks at about 11.7, 21.7, 23.2, 24.4±0.2 degrees two-theta comprising
a) providing crystalline oxcarbazepine having a PXRD diffraction pattern with peaks at about 11.9, 14.4, 20.0, 23.0, 25.1±0.2 degrees two-theta, b) maintaining the oxcarbazepine at a temperature in the range of from about 20 to about 30° C., and c) recovering the oxcarbazepine.

49. A process for preparing crystalline oxcarbazepine having a PXRD diffraction pattern substantially as depicted in FIG. 5 comprising:

a) contacting oxcarbazepine selected from the group consisting of crystalline oxcarbazepine having a PXRD diffraction pattern with peaks at about 11.9, 14.4, 20.0, 23.0, 25.1±0.2 degrees two-theta, crystalline oxcarbazepine having a PXRID diffraction pattern with peaks at about 11.7, 21.7, 23.2, 24.4±0.2 degrees two-theta, and crystalline oxcarbazepine having a PXRD diffraction pattern with peaks at about 11.7, 14.2, 24.3±0.2 degrees two-theta with a protic solvent; and b) recovering the oxcarbazepine.

50. The process of claim 49, wherein the crystalline oxcarbazepine is suspended in the protic solvent.

51. The process of claim 49, wherein the protic solvent is selected from the group consisting of water and ethanol.

52. The process of claim 50, wherein the crystalline oxcarbazepine is suspended in the protic solvent from about two hours to about three days.

53. The process of claim 52, wherein the crystalline oxcarbazepine is suspended for about one day.

54. A pharmaceutical composition comprising:

a) crystalline oxcarbazepine; and b) a pharmaceutically acceptable excipient, wherein the pharmaceutical composition is a solid pharmaceutical composition and wherein the crystalline oxcarbazepine is selected from the group consisting of crystalline oxcarbazepine having a PXRD diffraction pattern with peaks at about 11.9, 14.4, 20.0, 23.0, 25.1±0.2 degrees two-theta, crystalline oxcarbazepine having a PXRD diffraction pattern with peaks at about 11.7, 21.7, 23.2, 24.4±0.2 degrees two-theta, crystalline oxcarbazepine having a PXRD diffraction pattern with peaks at about 11.7, 14.2, 24.3±0.2 degrees two-theta, and crystalline oxcarbazepine chloroform solvate having a PXRD diffraction pattern with peaks at about 14.5, 15.0, 18.2, 21.4, 22.9, 24.0, 25.8, 26.0±0.2 degrees two-theta.

55. The pharmaceutical composition of claim 54, wherein the composition is mixed with one or more crystalline oxcarbazepine.

56. A pharmaceutical dosage form comprising the pharmaceutical composition of claim 54.

57. The pharmaceutical dosage form of claim 56, wherein the dosage form is a capsule or tablet.

58. The pharmaceutical dosage form of claim 57, wherein the dosage form is a tablet.

59. The pharmaceutical dosage form of claim 56, containing a unit dosage of about 150 mg to about 600 mg oxcarbazepine.

60. The pharmaceutical dosage form of claim 59, containing a unit dosage selected from the group consisting of about 150 mg, 300 mg and 600 mg.

61. A pharmaceutical dosage form comprising a pharmaceutical composition comprising:

a) crystalline oxcarbazepine; and b) a pharmaceutically acceptable excipient, wherein the crystalline oxcarbazepine is selected from the group consisting of crystalline oxcarbazepine having a PXRD diffraction pattern with peaks at about 11.9, 14.4, 20.0, 23.0, 25.1±0.2 degrees two-theta, crystalline oxcarbazepine having a PXRD diffraction pattern with peaks at about 11.7, 21.7. 23.2, 24.4±0.2 degrees two-theta, crystalline oxcarbazepine having a PXRD diffraction pattern with peaks at about 11.7, 14.2, 24.3±0.2 degrees two-theta, and crystalline oxcarbazepine chloroform solvate having a PXRD diffraction pattern with peaks at about 14.5, 15.0, 18.2, 21.4, 22.9, 24.0. 25.8, 26.0±0.2 degrees two-theta, and wherein the dosage form is an oral suspension.

62. The pharmaceutical dosage form of claim 61, wherein the dosage is about 60 mg ml$^{-1}$.

63. The pharmaceutical dosage form of claim 62, wherein the dosage is about 300 mg ml$^{-1}$.

64. A method of treating a patient suffering from seizures comprising administering the pharmaceutical composition of claim 54 to a patient in need thereof.

65. The method of claim 64, wherein the seizures are associated with epilepsy.

66. A method of treating Parkinson's disease comprising administering the pharmaceutical composition of claim 54.

67. A method of treating a patient suffering from seizures comprising administering the pharmaceutical composition of claim 61 to a patient in need thereof.

68. A method of treating Parkinson's disease comprising administering the pharmaceutical composition of claim 61.

* * * * *